(12) United States Patent
Sambusseti et al.

(10) Patent No.: US 10,052,187 B2
(45) Date of Patent: Aug. 21, 2018

(54) ORTHOTOPIC ARTIFICIAL BLADDER ENDOPROSTHESIS

(71) Applicants: Antonio Sambusseti, Cremona (IT); Gianni Cancarini, Brescia (IT)

(72) Inventors: Antonio Sambusseti, Cremona (IT); Gianni Cancarini, Brescia (IT)

( * ) Notice: Subject to any disclaimer, the term of this patent is extended or adjusted under 35 U.S.C. 154(b) by 19 days.

(21) Appl. No.: 15/037,915

(22) PCT Filed: Dec. 10, 2014

(86) PCT No.: PCT/IB2014/066754
§ 371 (c)(1),
(2) Date: May 19, 2016

(87) PCT Pub. No.: WO2015/087250
PCT Pub. Date: Jun. 18, 2015

(65) Prior Publication Data
US 2016/0287373 A1 Oct. 6, 2016

(30) Foreign Application Priority Data

Dec. 12, 2013 (IT) .......................... MI2013A002071

(51) Int. Cl.
*A61F 2/04* (2013.01)
*A61F 2/00* (2006.01)

(52) U.S. Cl.
CPC ............ *A61F 2/042* (2013.01); *A61F 2/0077* (2013.01); *A61F 2002/0086* (2013.01);
(Continued)

(58) Field of Classification Search
CPC .................... A61F 2/042; A61F 2/0077; A61F 2230/0023; A61F 2002/0086;
(Continued)

(56) References Cited

U.S. PATENT DOCUMENTS

2007/0276507 A1* 11/2007 Bertram .................. A61F 2/042
623/23.65

FOREIGN PATENT DOCUMENTS

WO     2007039159 A1    4/2007
WO     2007095193 A2    8/2007
(Continued)

OTHER PUBLICATIONS

Kuzmic et al. The Impact of Bladder Shape on the Ultrasonographic Measurement of Bladder Volume in Children. Pediatric Radiology 33.8 (2003):530-34.*

(Continued)

*Primary Examiner* — Christopher D Prone
*Assistant Examiner* — Rokhaya Diop
(74) *Attorney, Agent, or Firm* — Vorys, Sater, Seymour and Pease LLP

(57) ABSTRACT

An orthotopic artificial bladder endoprosthesis includes a base obtained with a multi-layered silicone membrane having an external surface and an internal surface both coated with pyrolytic turbostratic carbon; a resorbable cap obtained with a PGA fiber fabric, the base and the cap being connected with each other along respective edges, to define a closed enclosure; the base is connectable to the urethra and to the ureters of a patient; the base also being of substantially triangular form.

20 Claims, 2 Drawing Sheets

(52) U.S. Cl.
CPC ............... *A61F 2210/0004* (2013.01); *A61F 2210/0076* (2013.01); *A61F 2230/0023* (2013.01); *A61F 2250/006* (2013.01)

(58) Field of Classification Search
CPC ...... A61F 2210/0076; A61F 2210/0004; A61F 2250/006
See application file for complete search history.

(56) References Cited

FOREIGN PATENT DOCUMENTS

| WO | 20110018300 A1 | 2/2011 | | |
|---|---|---|---|---|
| WO | 2011064110 A1 | 6/2011 | | |
| WO | WO 2011064110 A1 * | 6/2011 | ............. | A61F 2/042 |
| WO | WO 2011160875 A1 * | 12/2011 | ............. | A61F 2/042 |

OTHER PUBLICATIONS

International Search Report and Written Opinion dated Mar. 26, 2015 for PCT/IB2014/066754 to Antonio Sambusseti filed Dec. 10, 2014.

* cited by examiner

ORTHOTOPIC ARTIFICIAL BLADDER ENDOPROSTHESIS

CROSS-REFERENCE TO RELATED APPLICATIONS

This is a § 371 National Stage Application of International Application No. PCT/IB2014/066754 filed on Dec. 10, 2014, claiming the priority of Italian Patent Application No. MI2013A002071 filed on Dec. 12, 2013.

The object of the present invention is an orthotopic artificial bladder endoprosthesis.

The application of the present invention lies in the replacement of a bladder of a patient, if the latter is suffering from serious incurable diseases that compromise correct bladder function.

Known bladder endoprostheses comprise a balloon casing made with a layered silicone membrane.

Such balloon is sufficiently rigid so as to stably keep its shape and flexible such that it can be manually compressed to ensure the emptying thereof.

The casing has a connection element located at a lower portion of the casing for the connection with the patient's urethra. Similarly, two connection bodies are located at the top to ensure the connection with the ureters.

These connections are achieved by suturing or by simply interlocking.

Several examples can be seen in the documents WO 2007/095193, WO 2011/064110 e WO 2011/018300.

Disadvantageously, the known bladder endoprostheses have several drawbacks.

Indeed, the endoprostheses of known type have a shape that is not entirely natural and this often causes problems in the flow of urine into and/or out of the same.

Indeed, it may often occur that during the expulsion of the urine, during the urination phase, part of the same flows back into the ureters, and from here towards the kidneys.

Clearly, this occurrence is entirely undesirable since it can cause kidney damage or infection.

In this context, the technical task underlying the present invention is to propose an orthotopic artificial bladder endoprosthesis that overcomes the drawback of the abovementioned prior art.

In particular, the object of the present invention is to provide an orthotopic artificial bladder endoprosthesis that allows a more natural functioning thereof and thus prevents possible kidney damage and/or infection.

The specified technical task and specified object are substantially achieved by an orthotopic artificial bladder endoprosthesis comprising the technical characteristics set forth in one or more of the enclosed claims.

Further characteristics and advantages of the present invention will be clearer from the non-limiting, exemplifying description of a preferred but not exclusive embodiment of an orthotopic artificial bladder endoprosthesis, as illustrated in the enclosed drawings in which.

Figure 1:
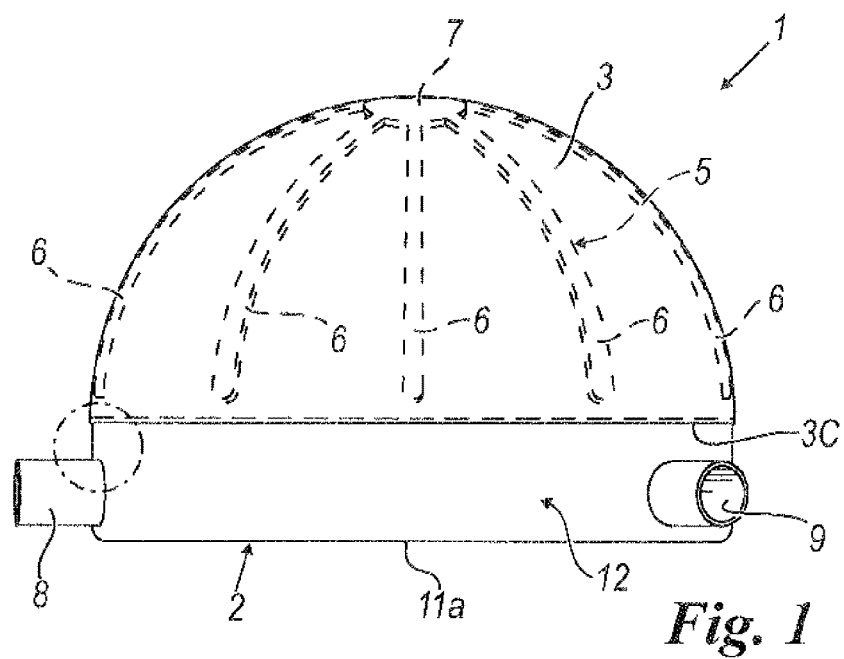
FIG. 1 is a side schematic view, partially in section, of an orthotopic artificial bladder endoprosthesis in accordance with the present invention.
Figure 2:
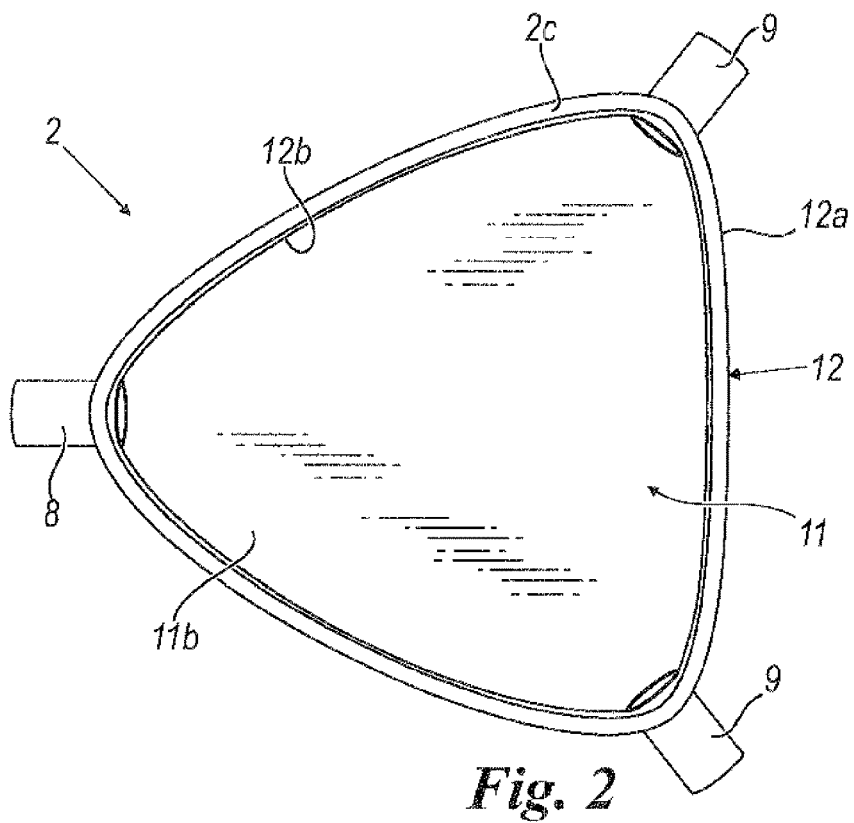
FIG. 2 is a plan view of a component of the endoprosthesis of FIG. 1.
Figure 3:
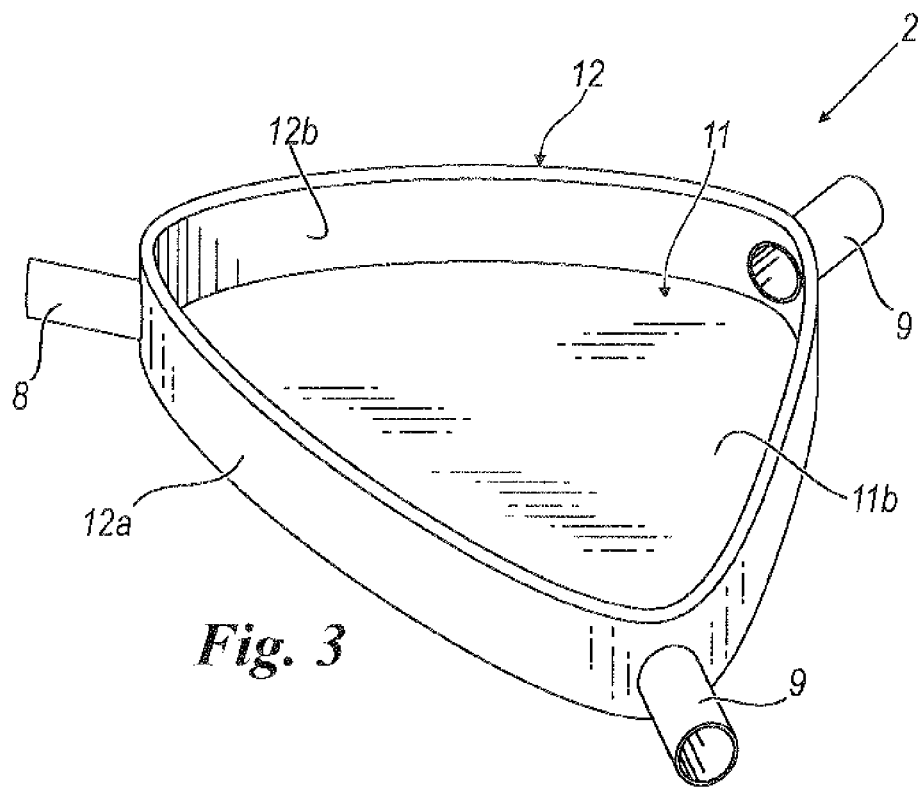
FIG. 3 is a perspective view of the component illustrated in FIG. 2.

With reference to the enclosed figures, reference number 1 overall indicates an orthotopic artificial bladder endoprosthesis in accordance with the present invention. The endoprosthesis 1 comprises a concave base 2 and a concave cap 3 connected together along respective edges 2c, 3c. In particular, the base 2 and the cap 3 are arranged in a manner such that the respective concavities are facing. In such a manner, between the base 2 and the cap 3, an enclosure 4 is defined for containing the patient's urine. The enclosure has a volume substantially comprised between 100 $cm^3$ and 900 $cm^3$, preferably being 400 $cm^3$.

The base 2 comprises a flat panel 11 and a wall 12 that is extended from the perimeter of the flat panel 11 and orthogonally thereto.

The base 2 has an external surface and an internal surface and is obtained with a multi-layered silicone membrane.

The external and internal surface of the base 2 are respectively formed by the external surface 11a and internal surface 11b of the flat panel 11 and by the external surface 12a and internal surface 12b of the wall 12.

The membrane of the base 2 has a thickness comprised between 500 μm and 700 μm; preferably the thickness of the membrane is substantially 600 μm.

In a preferred embodiment, the membrane comprises substantially 20 layers, each with thickness of about 30 μm.

In such a manner, the base 2 therefore has sufficient rigidity for maintaining its shape, while at the same time it is sufficiently flexible such that it can be pressed from the outside in order to facilitate the expulsion of the urine.

The membrane is produced by means of a process illustrated in the patent application WO 2007/039159, which is incorporated herein for reference purposes.

By way of example, the silicone used can be constituted by copolymers of dimethyl- and methyl vinyl-siloxane reinforced with silicon.

Advantageously, the silicone can be admixed with radio-opacifiers such as barium sulfate, titanium dioxide or the like, in a manner such that the endoprosthesis 1 can be detected by means of radiological diagnostic techniques.

Both on the external surface and on the internal surface of the base 2, respective layers are applied of a highly biocompatible protective material. By way of example, such material is pyrolytic turbostratic carbon with a thickness comprised between 0.2 μm and 0.3 μm.

The application of the carbon layer on the external surface of the base 2 allows preventing the risk that the forming fibrous capsule could adhere to the base 2. The application of the carbon layer on the internal surface of the base 2 allows protecting the base 2 from the corrosion caused by the urine.

The cap 3 has an external surface 3a and an internal surface 3b and is made with a fabric obtained by using an ultralight monofilament or thread deriving from PGA fibers (polyglycolide or poylglycolic acid), preferably homopolymer. PGA is a highly biocompatible and resorbable polymer and resistant to urine. Specifically, the resorption time of PGA is approximately one month. Advantageously, the use of PGA fibers in obtaining the fabric allows the formation of musculo-fibrous tissue outside the endoprosthesis 1. Inside, during resorption, there is the formation of a transition epithelium layer, which is also called urothelium. Advantageously, the urothelium layer is impermeable, an essential fact to ensure the correct functioning of the prosthesis and the neobladder that is being formed.

The fabric can be obtained by weaving the PGA thread in various ways, giving rise to a knitted fabric, a woven fabric or a non-woven fabric.

Preferably, the fabric is a knitted fabric, still more preferably a warp knitted fabric.

In this case, the fabric has a rougher surface capable of assuming a net configuration with sufficiently small meshes.

In detail, its weft is such that its interstitial space is less than 200 μm, preferably around 160 μm, corresponding to an average area of the holes equal to approximately 0.02 mm$^2$. This ensures impermeability to urine, preventing leaks.

Furthermore, the fabric is preferably textured so as to give it even greater surface roughness and greater rigidity and impermeability. The greater roughness of the fabric limits the risk of adhesion of the fibrous capsule.

Preferably, the endoprosthesis further comprises a frame 5 applied to the cap 3 in order to provide it with the necessary mechanical and structural characteristics. More precisely, the frame 5 is arranged on the internal surface 3b of the cap 3.

The frame 5 comprises plurality of arms 6 arranged as a star and defining a dome-like profile. More in detail, the arms 6 all have curved shape and are fixed together at a joining portion 7 located at the top of the cap 3. Preferably, the frame 5 is fixed to the fabric of the cap 3 by means of resorbable sutures.

Generally, the thickness of the frame 5, or of the arms 6 and the joining portion 7, is comprised between 0.1 mm and 10 mm, preferably between 0.5 mm and 2 mm. In a preferred embodiment, the thickness is substantially 1 mm.

The frame 5 is obtained by injection of a copolymer of lactic acid and glycolic acid, indicated as PGA/PLA (poly(lactic-co-glycolic) acid) whose domed shape is imparted when hot by means of thermoforming.

Since lactic acid is a chiral molecule, different types of polymer, PDLA, PLLA, PDLLA exist, where D and L represent the two stereoisomers. PLLA has a crystallinity of 37%, a vitreous transition temperature of between 50° C. and 80° C. and a melting temperature comprised between 173° C. and 178° C., whereas polymer deriving from the polymerization of a racemic mixture, PDLLA, is amorphous. The term poly(lactic) acid is here intended to identify all of the various abovementioned types of PLA.

The PGA/PLA copolymer, with which the frame 9 is made, is formed by a quantity of PGA comprised between 20% and 30% and by a quantity of PLA correspondingly comprised between 70% and 80%.

Particularly preferred as a PGA/PLA (poly(lactic-co-glycolic) acid) copolymer is the copolymer poly(L-lactic-co-glycolic) (PLLA/PGA) in which the L-lactic acid has a molar percent of 82-88% whereas glycolic acid has a molar percent of 18-12%. This copolymer is commercially known by the name of Resomer® LG855S.

It should be noted that the cap 3 obtained with the PGA fabric as described above, in particular textured, in combination with the PGA/PLA frame 5, shows a good mechanical consistency and sufficient rigidity, even in the presence of urine, and so is capable of ensuring a correct deformation of the bladder during emptying and/or filling thereof, at the same time showing a good resistance to leaks of urine.

Furthermore, the cap 3 and the frame 5 have proven to be neutral when in contact with growing neotissue. This involves a rapid population of the device by the cells of the surrounding growing tissue. At the same time, adhesion has proven to be limited due to the limited interaction between the polymers that comprise the cap 3 and the frame 5 and the biological molecules, thus ensuring a fusion with the patient's internal tissues. Hence, it follows that the base 2 is of permanent type, while the cap 3 is of resorbable type.

In accordance with the present invention, the base 2 has substantially triangular form in plan view.

In more detail, the plan form of the base 2 is an equilateral triangle. Preferably, the vertices are rounded.

In particular, the flat panel 11 of the base 2 has the form of an equilateral triangle.

By way of example, the side of the flat panel 11 has a length comprised between 3 cm and 6 cm, preferably between 4 cm and 5 cm.

In addition, the base 2 is connectable both to the urethra and to the ureters of a patient.

For such purpose, the base 2 comprises at least one first connector 8 for the connection of the base 2 with the urethra and to allow the exit of the urine from the containment enclosure 4.

In particular, the first connector 8 is fixed to the wall 12 of the base 2.

Similarly, the base 2 comprises at least two second connectors 9 for the connection of the base 2 with the ureters and to allow the entrance of the urine into the containment enclosure 4.

In particular, the second connectors 9 are fixed to the wall 12 of the base 2.

Merely by way of example, the first connector 8 and/or the second connectors 9 can comprise respective sleeves fixed to the wall 12 of the base 2 at respective openings.

By way of example, the sleeves of the first connector 8 and/or of the second connectors 9 can be obtained with a multi-layered silicone membrane coated with pyrolytic turbostratic carbon.

Preferably, the second connectors 9 are equidistant from the first connector 8.

Preferably, the distance between the first connector 8 and the second connectors 9 is equal to the distance between the second connectors 9.

By way of example, such distance is comprised between 3 cm and 6 cm, preferably between 4 cm and 5 cm.

As stated above, the base 2 and the cap 3 are connected at their respective edges 2c, 3c.

For such purpose, the base 2 comprises a band 10 embedded in the wall 12 in proximity of the edge 2c of the base 2 itself.

In particular, the band 10 is extended along the entire edge 2c of the base 2. Still more particularly, the band 10 is extended along the entire wall 12 of the base 2. The band 10 is made of biocompatible and preferably non-resorbable material.

The band 10 is fixed to the cap 3 at the edge 3c. In particular, the band 10 is fixed along the entire edge 3c of the cap 3.

Preferably, the band 10 is fixed to the cap 3 by means of sewing obtained with a resorbable thread. By way of example, such thread can be constituted by PGA.

Figure 4:
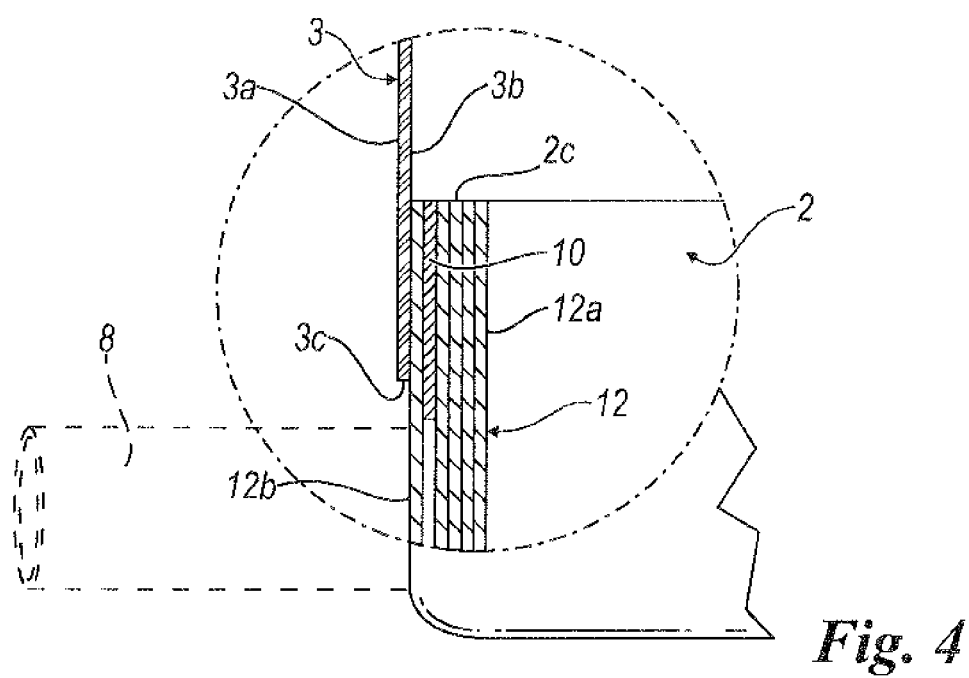
FIG. 4 is an enlarged section view of an enlarged detail of FIG. 1.

In the preferred embodiment, the band 10 is constituted by a fabric made of polyethylene terephthalate (using for example the product commercially known as Dacron®) and/or Goretex® fibers, or by a fabric constituted by polytetrafluoroethylene membranes. In accordance with that illustrated (FIG. 4), the band 10 is "embedded" in the membrane that constitutes the base 2. In other words, the band 10 is comprised between two adjacent silicone layers of the membrane. In particular, the band 10 is arranged between two layers located in proximity of the external surface of the base 2.

The band 10 has a height substantially equal to 0.5 cm. The invention thus described attains the pre-established object.

Indeed, the shape of the base and the fact that it is connected both to the urethra and to the ureters of the patient confer a more natural conformation to the endoprosthesis, close to that of the human bladder.

This allows more physiological flows of the urine and in particular prevents irregularities in the entrance and exit of the urine from the endoprosthesis itself.

Consequently, a return of the urine towards the kidneys is prevented, limiting or entirely preventing possible consequent damages.

The invention claimed is:

1. An orthotopic artificial bladder endoprosthesis comprising:
   a base having a multi-layered silicone membrane having an external surface and an internal surface both coated with pyrolytic turbostratic carbon;
   a resorbable cap having a PGA fiber fabric,
   said base and said cap being connected together along respective edges to define a closed enclosure;
   wherein said base is connectable to a urethra and to ureters of a patient, and
   wherein said base is of substantially triangular form.

2. The endoprosthesis according to claim 1, wherein said base has a substantially flat bottom wall and the closed enclosure is between the bottom wall and the resorbable cap.

3. The endoprosthesis according to claim 1, wherein said base comprises at least one first connector to connect said base to said urethra and at least two second connectors for connecting said base to said ureters.

4. The endoprosthesis according to claim 3, wherein said second connectors are equidistant from the first connector.

5. The endoprosthesis according to claim 1, wherein the base comprises a band projecting from said edge of the base and made of biocompatible, non-resorbable material; said band being fixed to the edge of the cap.

6. The endoprosthesis according to claim 5, wherein said band is embedded between two adjacent layers of the membrane at the external surface of the base.

7. The endoprosthesis according to claim 5, wherein said band is extended along the entire edge of the base.

8. The endoprosthesis according to claim 1, comprising a frame fixed to an internal surface of the cap; said frame comprising a plurality of arms arranged as a star and defining a dome-like profile, wherein the plurality of arms radiate from a joining portion so the arms diverge from each other to expose resorbable cap PGA fiber fabric between the arms.

9. The endoprosthesis according to claim 1, wherein the fabric of said cap is of warp knitted type.

10. The endoprosthesis according to claim 1, wherein the membrane of said base has a thickness between 500 μm and 700 μm.

11. The endoprosthesis according to claim 1, wherein the membrane of said base has a thickness of about 600 μm.

12. The endoprosthesis according to claim 1, wherein the fabric of said cap is textured.

13. The endoprosthesis according to claim 1, wherein the fabric of said cap is of warp knitted type and textured.

14. The endoprosthesis according to claim 1, wherein said base has sufficient rigidity for maintaining its shape, while at the same time is sufficiently flexible to be pressable from the outside to facilitate expulsion of urine.

15. The endoprosthesis according to claim 1, wherein the cap has cap sidewalls and the base has a bottom wall and base sidewalls and the cap sidewalls connect directly to the base sidewalls.

16. The endoprosthesis according to claim 1, wherein the cap has sidewalls, wherein the base has a flat panel lower wall and base sidewalls that extend from a perimeter of the flat panel lower wall and project orthogonally relative to the flat panel lower wall,
    wherein edges of the cap sidewalls connect directly to edges of the base sidewalls, and
    wherein the closed enclosure is between the flat panel lower wall and the resorbable cap and enclosed by the flat panel lower wall, the base sidewalls, and the resorbable cap.

17. The endoprosthesis according to claim 16, wherein the base comprises a band projecting from said edge of the base and made of biocompatible, non-resorbable material; said band being fixed to the edge of the cap.

18. The endoprosthesis according to claim 17, wherein said band is embedded between two adjacent layers of the membrane at the external surface of the base.

19. The endoprosthesis according to claim 18, comprising a frame fixed to an internal surface of the cap; said frame comprising a plurality of arms arranged as a star and defining a dome-like profile, wherein the plurality of arms radiate from a joining portion so the arms diverge from each other to expose resorbable cap PGA fiber fabric between the arms.

20. The endoprosthesis according to claim 19, wherein said band is extended along the entire edge of the base.

* * * * *